United States Patent [19]
Benson

[11] Patent Number: 5,392,973
[45] Date of Patent: Feb. 28, 1995

[54] TELEMETRY POUCH

[75] Inventor: Anthony B. Benson, Arlington, Tex.

[73] Assignee: Tecnol Medical Products, Inc., Fort Worth, Tex.

[21] Appl. No.: 127,781

[22] Filed: Sep. 27, 1993

[51] Int. Cl.⁶ ............................................. A45F 3/14
[52] U.S. Cl. .................................. 224/208; 224/202; 224/236; 224/901
[58] Field of Search .............. 224/208, 901, 202, 224, 224/235, 236, 908, 909, 910, 237; 128/644, 639, 903, 904, 379; 607/36; 206/284, 290, 363, 387, 438, 466, 84

[56] References Cited

U.S. PATENT DOCUMENTS

| | | | |
|---|---|---|---|
| 1,188,955 | 6/1916 | Leonard | 224/208 |
| 1,779,207 | 10/1930 | Candan | 222/237 |
| 4,069,955 | 1/1978 | Noyes | 224/208 |
| 4,411,267 | 10/1983 | Heyman | 224/224 |
| 4,637,535 | 1/1987 | Aleman | 224/202 |
| 4,674,664 | 6/1987 | Simon | 224/215 |
| 4,793,486 | 12/1988 | Konopka | 4/604 |
| 4,872,599 | 10/1989 | Hubberd et al. | 224/208 |
| 5,116,306 | 5/1992 | Zander | 224/202 |
| 5,121,864 | 6/1992 | Geschwind | 224/236 |

FOREIGN PATENT DOCUMENTS 18310 2/1907 United Kingdom ................ 2/49.2

*Primary Examiner*—Henry J. Recla
*Assistant Examiner*—Gregory M. Vidovich
*Attorney, Agent, or Firm*—Baker & Botts

[57] ABSTRACT

A telemetry pouch (12) is provided for maintaining a telemetry unit (14) adjacent a patient (10). The pouch (12) includes a transparent front wall (34) and a nonwoven material back wall (36) which are attached along a portion (38) of the periphery of the walls (34, 36). The transparent front wall (34) allows the telemetry unit (14) to be viewed during use. The pouch (12) additionally includes a flap (42) with a reactivating, resealable adhesive strip (46) for releasably covering the top opening (41) of the pouch (12). The pouch (12) may be secured to the patient (10) by straps (18, 20) or a clip (52).

7 Claims, 2 Drawing Sheets

TELEMETRY POUCH

TECHNICAL FIELD OF THE INVENTION

The present invention relates to medical apparatus, and more particularly to a pouch-like apparatus for removably securing a telemetry unit or the like to a patient.

BACKGROUND OF THE INVENTION

Telemetry monitoring has become widely used in the care of patients such as coronary patients. Many hospitals now have sophisticated equipment to continuously monitor the condition of a coronary patient by portable individual telemetry units and a centralized receiving and recording system.

Several types of telemetry pouches have been developed to attach a telemetry unit to a patient. One type of telemetry pouch provides two layers of an opaque polyolefin material secured about their periphery to form a pocket. This first type of telemetry pouch does not allow the telemetry equipment to be viewed without removal of the unit from the pouch. Additionally, the open top of the pouch allows moisture and contaminants to invade the pocket.

A second type of telemetry pouch provides a rigid foam, such as styrofoam, pouch with a small window cut in the front face of the pouch to allow viewing of a specified portion of a telemetry unit for which the pouch was designed. This pouch has some shortcomings. First, the rigid foam may be hot and uncomfortable to the patient. Second, the pertinent part of the telemetry unit may only be viewed when the specific type of telemetry unit for which the pouch was designed is used with the pouch.

Another type of telemetry pouch is formed of cloth material sewn at the edges and provided with straps to tie the pouch around the patient's neck. This type of pouch is not designed to prevent moisture from coming in contact with the pouch nor to allow viewing of the telemetry pouch during use.

Another type of telemetry pouch is formed of two non-breathable plastic sheets secured together to form a pocket with sealable top. This type of pouch resembles and functions like a ZIPLOC® brand freezer bag. Since this type of pouch does not allow air to permeate the bag and cool the telemetry unit, the pouch may become quite hot and uncomfortable for the patient to wear.

One example of prior telemetry pouches is shown in U.S. Pat. No. 4,872,599 entitled Telemetry Pouch with Expansible Chest Strip to Vance M. Hubbard and Welton K. Brunson. U.S. Pat. No. 4,872,599 is incorporated by reference for all purposes in this application.

SUMMARY OF THE INVENTION

The present invention provides a medical telemetry pouch that eliminates or substantially reduces the shortcomings of the prior art telemetry pouches. The present invention provides a telemetry pouch for holding a telemetry unit adjacent to a patient. The pouch may be formed with a clear front wall and a non-woven material back wall. The clear front wall allows the front of all telemetry units used with the pouch to be viewed. The pouch provides a flap having a reactivating, resealable adhesive strip for releasably securing the flap over the top opening of the pouch.

In accordance with one aspect of the present invention, a telemetry pouch is provided which can receive various types of telemetry units and allow full viewing of any telemetry unit contained within the pouch. The telemetry pouch is formed from selected materials which keep the telemetry unit dry and may allow air to permeate the pouch and cool the telemetry unit. These materials result in a pouch which is cooler for a patient to wear for extended periods of time. The pouch is also constructed from materials in an economical manner to allow the pouch to be disposable.

BRIEF DESCRIPTION OF THE DRAWINGS

A more complete understanding of the invention and its advantages will be apparent from the detailed description taken in conjunction with the accompanying Drawings in which.

DETAILED DESCRIPTION OF THE INVENTION

The preferred embodiment of the present invention and its advantages are best understood by referring to FIGS. 1–5 of the drawings, like numerals being used for like and corresponding parts of the various drawings.

Figure 1:
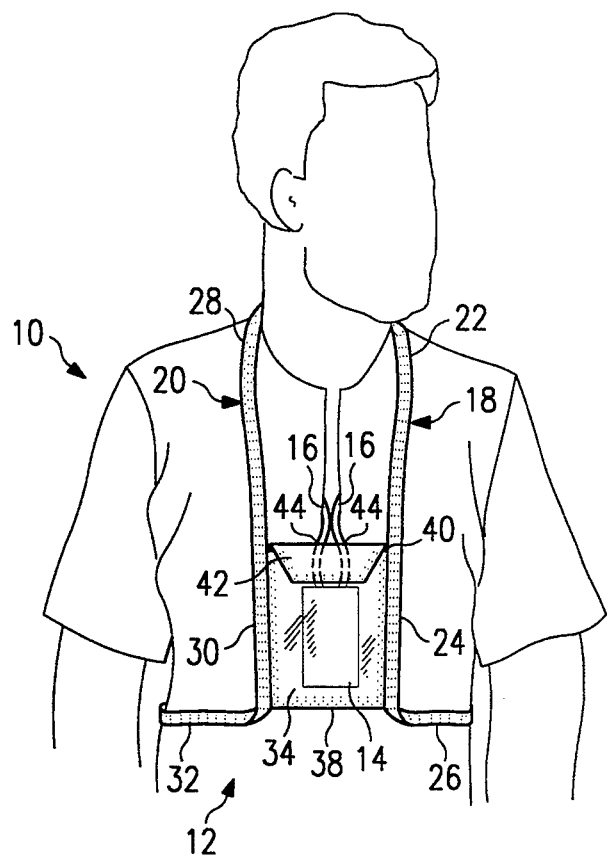
FIG. 1 is a schematic view of a first embodiment of the telemetry pouch of the present invention shown attached to the patient in a front position.
Figure 2:
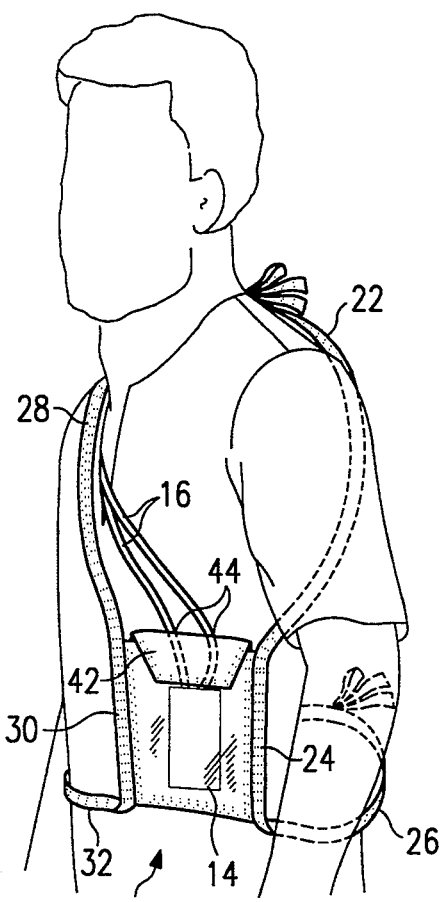
FIG. 2 is a schematic view of the telemetry pouch of FIG. 1 shown attached to the patient in a side position.

Referring to FIG. 1, patient 10 is fitted with pouch 12 in a front position. Telemetry unit 14, is connected to the patient by cables 16. Pouch 12 is secured to patient 10 by first strap 18 and second strap 20. First strap 18 has a first portion 22, a second portion 24 and a third portion 26. Likewise, second strap 20 has a first portion 28, a second portion 30 and a third portion 32. First portion 22 of first strap 18 and first portion 28 of second strap 20 may be tied behind the neck of patient 10. Third portion 26 of first strap 18 and third portion 32 of second strap 20 may be tied behind the back of patient 10. See FIG. 2. Pouch 12 may be positioned in a front position (FIG. 1) or a side position (FIG. 2). In this fashion, first strap 18 and second strap 20 provides securing means for securing pouch 12 to patient 10.

Telemetry unit 14 is held or maintained adjacent to patient 10 by pouch 12. When in position, telemetry unit 14 is visible through a front wall 34 of pouch 12. Front wall 34, preferably formed from transparent material, for example, a blown polypropylene, is attached to a back wall 36 formed of a non-woven material. The non-woven material of back wall 36 may be any light weight non-woven heat sealable material such as polyolefin, polypropylene, or hydro-entangled polyester. In the preferred embodiment, the non-woven material of back wall 36 is a spun bonded polyolefin such as TYVEK®, which is available from DuPont.

Front wall 34 and back wall 36 are attached along a first portion 38 of their periphery, but a second portion 40 is not attached. Second portion 40 defines a top opening 41 for receiving telemetry unit 14. Back wall 36 may have a flap extension 42 coupled to back wall 36. Flap extension 42 is formed to fold and cover top opening 41. Flap extension 42 contains at least one cable opening 44 for allowing cables 16 to pass to monitoring sites (not shown) on patient 10.

Figure 3:
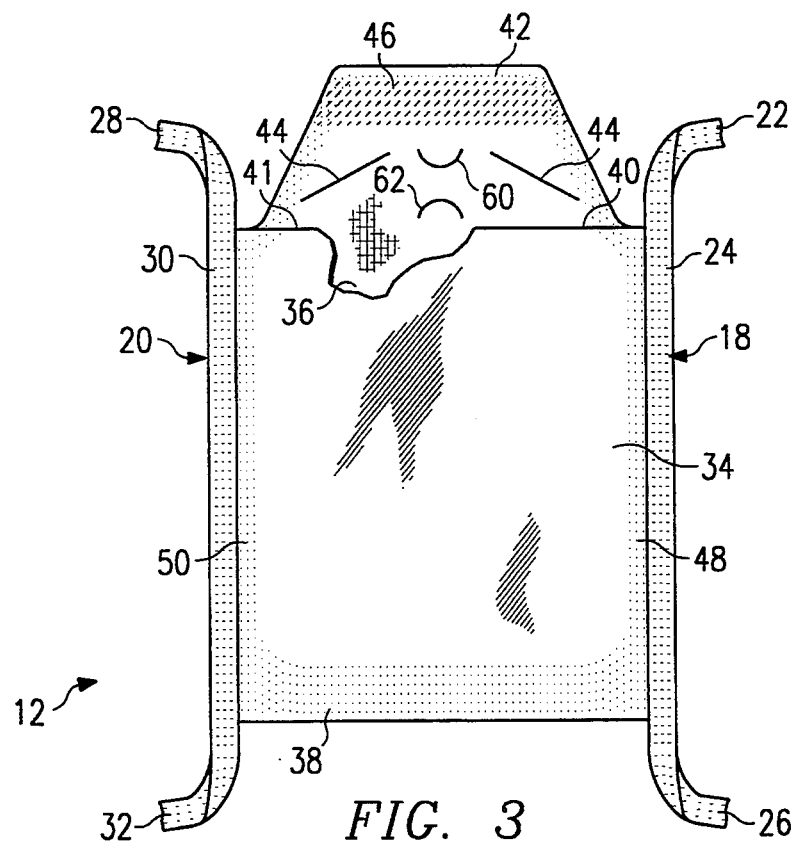
FIG. 3 is an elevational view with portions broken away showing a central portion of the telemetry pouch of FIGS. 1 and 2.

Referring to FIG. 3, there is shown a schematic view of a central portion of pouch 12 shown in FIGS. 1 and 2. Flap extension 42 is shown in an open position; in this position, reactivating, resealable adhesive strip 46 is visible. Adhesive strip 46 allows flap extension 42 to be non-releasably secured to transparent front wall 34 once telemetry unit 14 is placed within the pocket formed by front wall 34 and back wall 36. Reactivating, resealable adhesive strip 46 may be, for example, fastener tape available from the 3M Company (Product No. 9920). Cable openings 44 may be formed as slots in flap extension 42. Front wall 34 and back wall 36 may be ultrasonically bonded along first portion of periphery 38 of walls 34 and 36. A second portion of periphery 40 defines top opening 41 of pouch 12. Once a pocket is formed by front wall 34 and back wall 36, various types of securing means may be attached to allow the pouch to be secured to patient 10.

One securing means is straps 18 and 20. Second portion 24 of first strap 18 may be ultrasonically bonded or bonded by other means known in the art such as bonding by heat and pressure or by stitching with thread to first edge 48 of the periphery of front wall 34 and back wall 36. Strap portion 24 may be folded about its length to encase walls 34 and 36 along edge 48 and then attached by means known in the art such as thermal bonding or ultrasonic bonding. Likewise, second portion 30 of second strap 20 may be attached by means known in the art such as ultrasonically bonding to second edge 50 of the periphery formed by front wall 34 and back wall 36. Strap portion 30 may be folded about its length to encase walls 34 and 36 along edge 50 and then attached.

Figure 4:
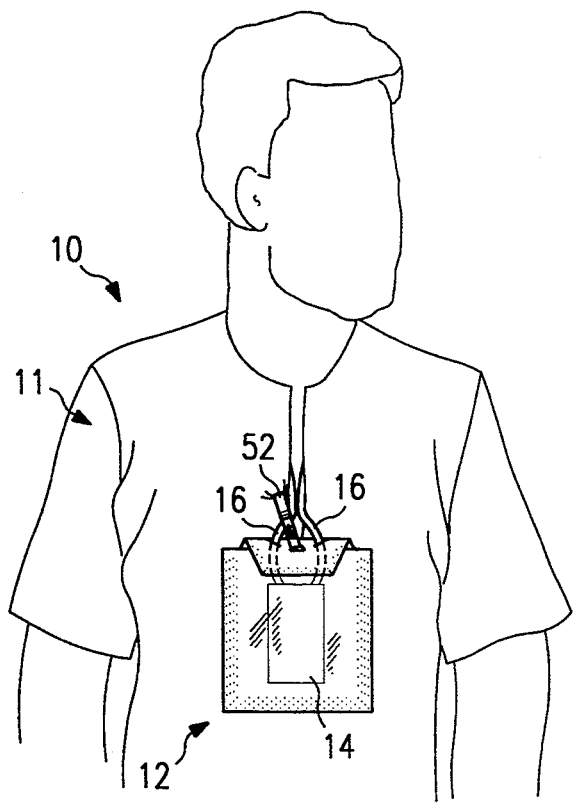
FIG. 4 is a schematic view of a second embodiment of the telemetry pouch of the present invention shown attached to the patient in the front position.
Figure 5:
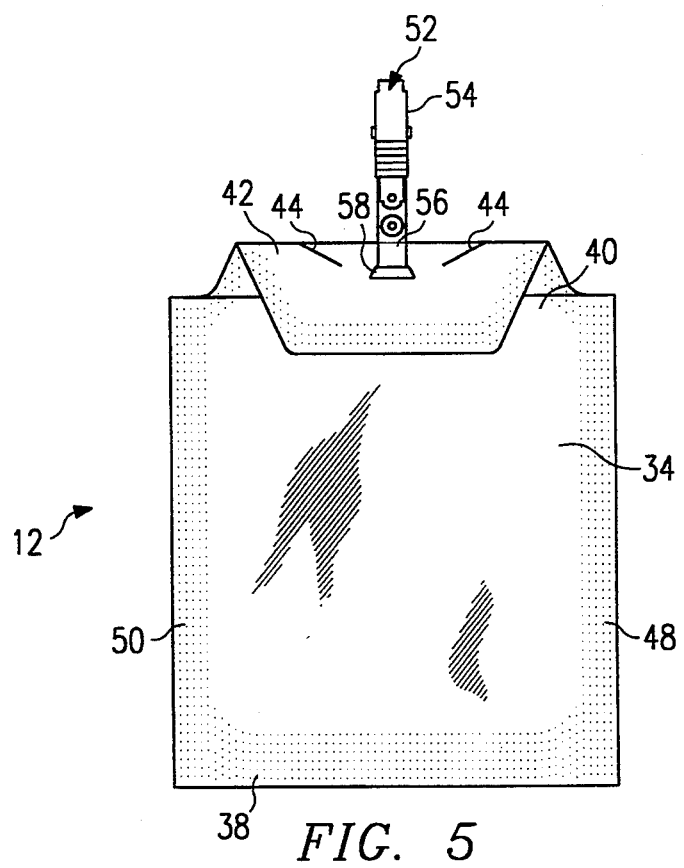
FIG. 5 is an elevational view of the telemetry pouch shown in FIG. 4.

An alternative embodiment of pouch 12 showing an alternative securing means is shown in FIGS. 4 and 5. Referring to FIG. 4, pouch 12 is shown secured to garment 11 of patient 10. Referring to FIG. 5, clip 52 is shown secured to pouch 12. Clip 52 may have alligator jaws 54 for gripping garment 11 and loop 56 for securing pouch 12 to clip 52. Loop 56 of clip 52 is passed through clip opening 58. Clip opening 58 may be formed by a first clip opening 60 and a second clip opening 62 on flap extension 42 as shown in FIG. 3. In other respects, the embodiment shown in FIGS. 4 and 5 is substantially the same as the embodiment shown in FIGS. 1 through 3.

In manufacturing pouch 12, the manufacturer may provide a transparent front wall 34 such as a clear plastic film, and a back wall 36. The manufacturer may then attach a first portion 38 of the periphery of walls 34 and 36 to form a pocket for receiving telemetry unit 14. The manufacturer may couple to back wall 36 or form as an integral part thereof, flap extension 42. A reactivating, resealable adhesive strip 46 is applied to flap extension 42 and cable openings 44 are created. If the securing means is to be clip 52, first and second clip openings 60 and 62 are formed in flap 42. First and second clip openings 60 and 62 may be semicircular openings to distribute forces along a greater length. A securing means may then be attached to front wall 34 and back wall 36.

If the securing means is clip 52, loop 56 may be passed through opening 58 formed by first and second clip openings 60 and 62. If the securing means is to be straps 18 and 20, second portion 24 of first strap 18 is then attached to first edge 48 of the periphery of walls 34 and 36. Second portion 30 of second strap 20 may then be attached to second edge 50 of the periphery of walls 34 and 36. Portions 24 and 30 may be secured by any means known in the art, but in the preferred embodiment are ultrasonically bonded. With this latter securing means, the first portions of straps 18 and 20 may then be tied behind the neck of patient 10, and the third portion of straps 18 and 20 may be tied about the waist or torso of patient 10. Straps 18 and 20 may be formed of a nonwoven material. To strengthen straps 18 and 20, each strap may be folded lengthwise, the second portion 24 or 30 may be aligned to encase first or second edge 48 or 50 of portion 38 of the periphery of walls 34 and 36. Alternatively, each strap may be folded over on itself and ultrasonically bonded about its length before being attached to edge or portions 38 and 40.

To use pouch 12, telemetry unit 14 is inserted through top opening 41 into pouch 12. Cables 16 are then passed through cable openings 44, and flap extension 42 may be folded over towards front wall 34 and adhesive 46 may engage front wall 34. Transparent front wall 34 allows telemetry unit 14 to be viewed during use in pouch 12. Back wall 36, which is made of a relatively cool backing material is placed against patient 10. Pouch 12 is then secured to patient 10 by a securing means. If the embodiment of FIGS. 1 through 3 is used, straps 18 and 20 are tied around patient 10 as previously described. If the embodiment of FIGS. 4 and 5 is used, pouch 12 is secured with clip 52.

Although the present invention and its advantages have been described in detail, it should be understood that various changes, substitutions and alterations can be made therein without departing from the spirit and scope of the invention as defined by the appended claims.

What is claimed is:

1. A pouch for maintaining a telemetry unit adjacent to a patient, the pouch comprising:
   a transparent front wall;
   a back wall, the back wall attached to the front wall along a first portion of the periphery of the front and back walls and a second portion of the periphery forming a top opening for receiving the telemetry unit;
   a flap extension coupled to the back wall proximate the top opening, the flap extension having at least one cable opening therein;
   a reactivating, resealable adhesive strip provided on the flap extension for releasably attaching the flap to the front wall;
   securing means for releasably securing the pouch to the patient; and
   wherein the securing means comprises:
      a first strap having a first, second, and third portion, the second portion of the first strap attached to a first edge of the front and back walls,
      a second strap having a first, second, and third portion, the second portion of the second strap attached to a second edge of the front and back walls,
      the first portion of the first strap and the first portion of the second strap sized to pass around the patient's neck and to be secured to each other, and
      the third portion of the first strap and the third portion of the second strap sized to pass around the patient's torso and to be secured to each other.

2. A telemetry pouch for maintaining a telemetry unit adjacent to a patient, the telemetry pouch comprising:
- a transparent front wall for viewing the telemetry unit;
- a back wall formed of a light weight non-woven material, the back wall attached to the front wall along a first portion of the periphery of the front and back walls and a second portion forming a top opening for receiving the telemetry unit;
- a flap extension coupled to the back wall proximate the top opening, the flap extension having at least one cable opening therein;
- a reactivating, resealable adhesive strip provided on the flap extension for releasably attaching the flap to the front wall;
- a first strap having a first, second, and third portion, the second portion of the first strap attached to a first edge of the transparent front wall and the back wall;
- a second strap having a first, second, and third portion, the second portion of the second strap attached to a second edge of the transparent front wall and the back wall;
- the first portion of the first strap and the first portion of the second strap adapted for tying about the patient's neck; and
- the third portion of the first strap and the third portion of the second strap adapted for tying about the patient's torso.

3. The telemetry pouch of claim 2, wherein the first and second strap comprise a non-woven material.

4. The telemetry pouch of claim 2, wherein the first and second strap comprise a polypropylene material.

5. The telemetry pouch of claim 2, wherein each of the first and second straps comprises a non-woven strap folded lengthwise and bonded about its length.

6. A method of manufacturing a telemetry pouch for holding a telemetry unit adjacent to a patient, the steps comprising:
- providing a transparent front wall;
- providing a back wall formed of a non-woven material;
- attaching the transparent front wall and the back wall to form a pocket having a top opening:
- providing a flap extension on the back wall for folding over the top opening;
- forming a cable opening in the flap extension for passing cables from monitoring sites to the telemetry unit;
- providing a reactivating, resealable adhesive strip on the flap for releasably securing the flap to the transparent front wall; and
- providing a securing means coupled to the pouch for securing the pouch to the patient wherein the step of providing a securing means comprises the steps of:
  - providing a first strap having a first, second, and third portion,
  - providing a second strap having a first, second, and third portion,
  - attaching the second portion of the first strap to a first edge of the front and back walls, and
  - attaching the second portion of the second strap to a second edge of the front and back walls.

7. The method of claim 6 further comprising the steps of:
- folding the first strap along the length of the first strap;
- bonding the first strap along its length after the first strap has been folded over on itself to encase the first edge of the front and back walls;
- folding the second strap along the length of the second strap; and
- bonding the second strap along its length after the second strap has been folded over along the second strap's length to encase a portion of the second edge of the front and back walls.

* * * * *